US010265002B2

(12) United States Patent
Elliott et al.

(10) Patent No.: US 10,265,002 B2
(45) Date of Patent: Apr. 23, 2019

(54) NON-INVASIVE BLOOD ANALYSIS

(71) Applicant: Leman Micro Devices SA, Lausanne (CH)

(72) Inventors: Christopher Elliott, St. Sulpice (CH); Mark-Eric Jones, Cossonay-Ville (CH); Arushi Varshney, Lausanne (CH); Matthieu Ruegg, Lausanne (CH)

(73) Assignee: LEMAN MICRO DEVICES SA, Lausanne (CH)

( * ) Notice: Subject to any disclaimer, the term of this patent is extended or adjusted under 35 U.S.C. 154(b) by 656 days.

(21) Appl. No.: 14/767,772

(22) PCT Filed: Feb. 10, 2014

(86) PCT No.: PCT/IB2014/000139
§ 371 (c)(1),
(2) Date: Aug. 13, 2015

(87) PCT Pub. No.: WO2014/125355
PCT Pub. Date: Aug. 21, 2014

(65) Prior Publication Data
US 2016/0015301 A1    Jan. 21, 2016

(30) Foreign Application Priority Data

Feb. 13, 2013  (GB) .................................. 1302548.1
Sep. 23, 2013  (GB) .................................. 1316914.9
Sep. 23, 2013  (GB) .................................. 1316915.6

(51) Int. Cl.
*A61B 5/1455*    (2006.01)
*A61B 5/145*     (2006.01)
(Continued)

(52) U.S. Cl.
CPC .......... *A61B 5/1455* (2013.01); *A61B 5/0205* (2013.01); *A61B 5/0261* (2013.01);
(Continued)

(58) Field of Classification Search
CPC ... A61B 5/0205; A61B 5/0059; A61B 5/1455; A61B 5/14551; A61B 5/14552;
(Continued)

(56) References Cited

U.S. PATENT DOCUMENTS 4,882,492 A     11/1989  Schlager
5,007,423 A *    4/1991  Branstetter ........ A61B 5/14551
                                                        600/334
(Continued)

FOREIGN PATENT DOCUMENTS

CN    101484065 A    7/2009
CN    202235386 U    5/2012
(Continued)

OTHER PUBLICATIONS

Notification of Transmittal of the International Preliminary Report on Patentability for corresponding PCT application PCT/IB2014/000139, dated Jan. 26, 2015, 14 pages.
(Continued)

*Primary Examiner* — Eric Winakur
*Assistant Examiner* — Chu Chuan (JJ) Liu
(74) *Attorney, Agent, or Firm* — J. Clinton Wimbish; Nexsen Pruet, PLLC

(57) ABSTRACT

The present invention provides a personal hand-held monitor (PHHM) comprising a signal acquisition device for acquiring signals which can be used to derive a measurement of a parameter related to the health of the user, wherein the signal acquisition device comprises a blood photosensor having one or more photo-emitters for transmitting light to a body part of a user, one or more photo-detectors for detecting light transmitted through or scattered by the body part and two or more optical cells, at least one of which contains an analyte to be detected or which mimics the absorption spectrum of the analyte, through which the light
(Continued)

that has been or will be transmitted through or scattered by the body part passes before it reaches the photo-detector(s).

16 Claims, 3 Drawing Sheets

(51) Int. Cl.
    *A61B 5/022*     (2006.01)
    *A61B 5/026*     (2006.01)
    *A61B 5/00*     (2006.01)
    *A61B 5/0205*     (2006.01)
    *A61B 5/024*     (2006.01)
    *A61B 5/0245*     (2006.01)

(52) U.S. Cl.
    CPC ...... *A61B 5/02233* (2013.01); *A61B 5/14532* (2013.01); *A61B 5/14546* (2013.01); *A61B 5/14557* (2013.01); *A61B 5/489* (2013.01); *A61B 5/6897* (2013.01); *A61B 5/6898* (2013.01); *A61B 5/742* (2013.01); *A61B 5/7405* (2013.01); *A61B 5/0245* (2013.01); *A61B 5/02427* (2013.01); *A61B 2560/0425* (2013.01); *A61B 2562/0238* (2013.01)

(58) Field of Classification Search
    CPC ..... A61B 5/14532; A61B 5/72; A61B 5/6801; A61B 5/6813; A61B 5/6826; A61B 5/6838; A61B 5/02427; A61B 5/14546; A61B 5/02233; A61B 5/0261; A61B 5/6897; A61B 5/6898; A61B 5/7405; A61B 5/742; A61B 5/14557; A61B 5/0245
    See application file for complete search history.

(56) References Cited

U.S. PATENT DOCUMENTS

| | | | | |
|---|---|---|---|---|
| 5,137,023 A | * | 8/1992 | Mendelson | A61B 5/14532 600/316 |
| 5,190,041 A | | 3/1993 | Palti | |
| 5,511,546 A | * | 4/1996 | Hon | A61B 5/02444 600/310 |
| 5,638,816 A | * | 6/1997 | Kiani-Azarbayjany | A61B 5/14532 356/39 |
| 5,865,755 A | | 2/1999 | Golub | |
| 5,910,109 A | * | 6/1999 | Peters | A61B 5/14532 600/316 |
| 6,223,063 B1 | * | 4/2001 | Chaiken | A61B 5/02427 600/310 |
| 2004/0199061 A1 | * | 10/2004 | Glukhovsky | A61B 1/00188 600/312 |
| 2005/0137469 A1 | * | 6/2005 | Berman | A61B 5/14532 600/316 |
| 2005/0216654 A1 | | 9/2005 | Barth et al. | |
| 2005/0234312 A1 | | 10/2005 | Suzuki et al. | |

FOREIGN PATENT DOCUMENTS

| | | |
|---|---|---|
| JP | 2009233284 A | 10/2009 |
| JP | 2015-556584 | 11/2017 |
| RU | 2511278 C2 | 6/2012 |
| WO | 2013001265 A2 | 1/2013 |

OTHER PUBLICATIONS

International Search Report for corresponding PCT application PCT/IB2014/000139, dated May 21, 2014, 2 pages.
First Office Action, Chinese Patent Application No. 201480008599.1, dated Mar. 3, 2017, 12 pages.
Second Office Action, Chinese Patent Application No. 201480008599.1, dated Aug. 23, 2017, 8 pages.
Third Office Action, Chinese Patent Application No. 201480008599.1, dated Mar. 15, 2018, 7 pages.
Office Action related to Russian Patent Application No. 2015138985, dated Jan. 15, 2018, 11 pages.
Danaei, Goodarz et al., National, regional, and global trends in fasting plasma glucose and diabetes prevalence since 1980: systematic analysis of health examination surveys and epidemiological studies with 370 country-years and 2.7 million participants, www.thelancet.com, Jul. 2, 2011, vol. 378, pp. 31-40.
World Health Organization, Global Status Report on Noncommunicable Diseases 2010, ISBN 978 92 4 156422 9, 164 pages.
Klonoff, Noninvasive Blood Glucose Monitoring, PubMed—NCBI, 2 pages.
Fine, Ilya, Glucose Correlation with Light Scattering Patterns, Elfi-Tech Ltd., Science Park, Rehovot, Israel, 44 pages.

\* cited by examiner

NON-INVASIVE BLOOD ANALYSIS

CROSS REFERENCE TO PRIORITY APPLICATIONS

This application is a U.S. National Phase of PCT/IB2014/000139, filed Feb. 10, 2014, which claims the benefit of Great Britain Application No. 1302548.1, filed Feb. 13, 2013, Great Britain Application No. 1316914.9, filed Sep. 23, 2013, and Great Britain Application No. 1316915.6, filed Sep. 23, 2013, each of which are incorporated by reference in their entireties.

FIELD OF THE INVENTION

The present invention relates to a personal hand-held monitor (PHHM) adapted to measure the concentration of an analyte in blood.

BACKGROUND TO THE INVENTION

There are many circumstances in which it is desirable to measure the concentration of an analyte in blood. One of the most important is the measurement of blood glucose concentration, of crucial importance to the management of diabetes. It is estimated by Danaei et al. ("*National, regional, and global trends in fasting plasma glucose and diabetes prevalence since* 1980: *systematic analysis of health examination surveys and epidemiological studies with* 370 *country-years and* 2.7 *million participants*", Lancet, 2011, 378(9785):31-40) that 370 million people in the world suffer from diabetes and the WHO predicts that diabetes will be the 7th leading cause of death in 2030 ("*Global status report on non-communicable diseases* 2010", WHO 2011). At present, the only accurate and inexpensive way for diabetics to measure their blood glucose concentration is by taking a blood sample, usually by pricking a finger, and placing a drop of blood on a test strip. A measurement of the change of colour of the strip or a measurement of a redox reaction on the strip after application of the blood sample provides an indication of the blood glucose concentration.

Inexpensive automated equipment exists to estimate the change in colour or the electrochemical reaction but there is no consumer equipment capable of making the measurement without taking a blood sample and many diabetics have to do this several times per day.

Other analytes such as alcohol, haemoglobin, creatinine, cholesterol, stimulants or other drugs, including illegal or otherwise forbidden substances, are also important and again there is no accurate, reliable and inexpensive way of estimating their concentration non-invasively.

In principle, absorption spectroscopy would be a good method for estimating the concentration of an analyte but this is difficult in vivo if the contribution to the absorption from the analyte is small compared to the absorption by other materials in the blood and tissue, especially if the analyte has few or no narrow absorption bands in the useable near infra-red (NIR) and/or if those bands are overlapping with those of water, which is the predominant component of blood and tissue. For example, Klonoff ("*Non-invasive blood glucose monitoring*", Diabetes Care, 20, 3, 435-437 1997) states: "Glucose is responsible for <0.1% of NIR absorbed by the body. Water, fat, skin, muscle and bone account for the vast majority of NIR absorption. Perturbations in the amounts of these substances can alter NIR absorption and thus invalidate the calibration formula for correlating light absorption with blood glucose concentrations . . . ".

Even if this could be overcome, the measurement of the specific absorption would require a precise spectrometer that is not easily made inexpensively and reliably.

U.S. Pat. No. 4,882,492 in 1989 disclosed an invention employing "non-dispersive correlation infra-red spectroscopy". According to this disclosure, broad spectrum NIR light is transmitted through or scattered by a body part. The emergent light is split into two beams. One beam passes through a filter consisting of a solution of the analyte and the other through a neutral density filter. The analyte filter absorbs from the first beam substantially all of the light in the spectral absorption bands of the analyte. The neutral density filter reduces the power of the second beam to be similar to the power of the first beam. Any difference between the powers of the light in the two beams arises solely from the amount of light absorbed by the analyte in the body part.

The US patent alleges that spectral specificity is achieved without the need for a dispersive element (a spectrometer) but this depends crucially on the balance between the two beams and the exact characteristics of the neutral density filter. It also does not distinguish analyte in the blood from analyte in the surface layers of the tissue. In practice, this is likely to prevent the device ever being reliable or accurate.

Fine (Chapter 9 of Handbook of optical sensing of glucose in biological fluids and tissues, 2009) describes a technique for estimating glucose concentration by the change in the optical scattering of aggregated red blood cells. It uses an analogy with a pulse oximeter and correlates the scattered signal with the variation of area of the artery as the heart beats, thus making the signal preferentially sensitive to the glucose in the arterial blood. However, Fine concludes that this technique is ineffective, in part because the change in arterial area is relatively small.

WO 2013/001265 discloses significant improvements on U.S. Pat. No. 4,882,492. Claim 25 of WO 2013/001265 relates a personal hand-held monitor (PHHM) comprising a signal acquisition device for acquiring signals which can be used to derive a measurement of a parameter related to the health of the user, the signal acquisition device being integrated with a personal hand-held computing device (PHHCD), wherein the signal acquisition device comprises a blood photosensor having a photo-emitter for transmitting light to a body part of a user, a photo-detector for detecting light transmitted through or scattered by the body part and an optical cell, containing an analyte to be detected, through which light transmitted through or scattered by the body part passes before it reaches the photo-detector, wherein the processor of the PHHM is adapted to process signals obtained from the photo-detector in the presence of the body part and in the absence of the body part to provide a measurement of the concentration of the analyte in the user's blood. WO 2013/001265 also discloses using the principle of two beams, one of which passes through a cell containing the analyte and compares the power in each beam.

FIGS. 1 and 2 in the attached drawings, which are identical to FIGS. 9 and 11 of WO 2013/001265, show two arrangements of blood photosensors to be used in the PHHM claimed in claim 25 of WO 2013/001265, which may be incorporated into a PHHCD, or may be connected to a PHHCD or may be constructed as a stand-alone device with its own user interface, power supply and other electronic and mechanical components.

As shown in FIG. 1, a photo-emitter (81) transmits a beam of light that passes through a filter (82) to select the spectral band of the light to be used. The spectral band is chosen to allow inexpensive components and materials to be used whilst maximising the sensitivity and discrimination with respect to the analyte. The beam is collimated by a lens (83) to shine through a body part, such as a finger (84). A beam splitter (85) divides the beam between a non-analyte cell (86) and analyte cell (87). Photo-detectors (88) measure the intensity of the beam after it has passed through each cell. A differential amplifier may be used to amplify the difference in signals from the two photo-detectors.

FIG. 2 shows another arrangement in which the photo-emitter and photo-detector are on the same side of a body part, the photo-detector being sensitive to the light scattered back from the body part. A moving mirror (101) reflects light sequentially to each of two fixed mirrors (102) and hence to the non-analyte cell (86) or analyte cell. The photo-detector (108) measures the intensity of the beam that has passed the cells.

In each of these arrangements, the difference between the intensity when the beam of light has passed through the non-analyte cell and through the analyte cell is a measure of the amount of absorption by the analyte within the body part.

The invention disclosed in WO 2013/001265 goes some way towards the goal of a sensor that is non-invasive, inexpensive, accurate and reliable. However, it is not specific to the analyte contained in blood because the signal is also affected by analyte in the surrounding tissue. Further improvements are also desirable to reduce the cost of implementation and to improve accuracy.

THE PRESENT INVENTION

The present invention greatly improves on the performance of the PHHM of claim 25 of WO 2013/001265. It exploits more effectively a second degree of correlation to improve specificity.

According to a first aspect, the present invention provides a personal hand-held monitor (PHHM) comprising a signal acquisition device for acquiring signals which can be used to derive a measurement of a parameter related to the health of the user, the signal acquisition device being integrated with a personal hand-held computing device (PHHCD), wherein the signal acquisition device comprises a blood photosensor having one or more photo-emitters for transmitting light to a body part of a user, one or more photo-detectors for detecting light transmitted through or scattered by the body part and two or more optical cells, at least one of which contains an analyte to be detected or which mimics the absorption spectrum of the analyte to be detected, through which the light that has been or will be transmitted through or scattered by the body part passes before it reaches the or each photo-detector, wherein the processor of the PHHM is adapted to process the signals received from the or each photo-detector to calculate the difference in intensity of light which has passed through the or each analyte cell and light which has passed through the or each non-analyte cell and to process signals obtained from the photosensor in the presence of the body part and in the absence of the body part to provide a measurement of the concentration of the analyte in the user's blood.

Preferably, the processor of the PHHM of the first aspect of the invention is adapted to determine the pulse of the user and to correlate the signals obtained from the photosensor with the user's pulse in providing a measurement of the analyte in the user's blood. The processor of the PHHM may be adapted to analyse the signals received from the blood photosensor to determine the pulse of the user. Alternatively, the PHHM may include an electrical sensor comprising at least a first and a second electrode which are electrically isolated from one another and which are arranged to be contacted by two separate parts of the user's body, such as a finger on one hand and a finger on the other hand, and the processor of the PHHM is adapted to analyse the signals from the electrical sensor to determine the pulse of the user. Such an electrical sensor is disclosed in WO 2013/001265.

According to a second aspect, the present invention provides a personal hand-held monitor (PHHM) comprising a signal acquisition device for acquiring signals which can be used to derive a measurement of a parameter related to the health of the user, wherein the signal acquisition device comprises a blood photosensor having one or more photo-emitters for transmitting light to a body part of a user, one or more photo-detectors for detecting light transmitted through or scattered by the body part and two or more optical cells, at least one of which contains an analyte to be detected or which mimics the absorption spectrum of the analyte to be detected, through which the light that has been or will be transmitted through or scattered by the body part passes before it reaches the or each photo-detector, wherein the processor of the PHHM is adapted to process the signals received from the or each photo-detector to calculate the difference in intensity of light which has passed through the or each analyte cell and light which has passed through the or each non-analyte cell, to determine the pulse of the user and to correlate the signals obtained from the photosensor in the presence of the body part and in the absence of the body part with the user's pulse to provide a measurement of the concentration of the analyte in the user's blood.

In this aspect of the invention, the processor of the PHHM may be adapted to analyse the signals from the blood photosensor to determine the pulse or the PHHM may include an electrical sensor as referred to above.

Preferably, the PHHM of the second aspect of the invention is self-contained and includes a processor, display and control, communications and storage means to provide a measurement of the concentration of the analyte in the user's blood. Alternatively, the signal acquisition device is integrated with a personal hand-held computing device (PHHCD).

Preferably, in order further to improve the selectivity for the concentration of the analyte in blood, the processor of the PHHM is adapted to measure the intensity of a beam of light for use in photoplethysmography (PPG) to identify the time at which an artery in the body part dilates due to systole. The change in absorption at this point is a consequence solely of the additional amount of blood in the body part. FIG. 5, which illustrates this relationship, shows a graph derived from a mathematical model of the performance of this preferred feature. The horizontal axis is the concentration of the analyte, in this case illustrated as glucose, in the blood and the vertical axis is the change in difference of signal between the two cells when the artery is occluded and when the artery is patent, using a realistic value for the intensity of light from the photo-emitter and the scattering within the body part.

This change in difference of signal is proportional to the total amount of analyte, such as glucose, in the blood within the field of view of the PHHM. In FIG. 5, typical values for arterial size have been assumed. In order to convert this to a concentration, the PHHM is also adapted to estimate the volume of that additional blood from the intensity change of the beam of light.

Preferably, each photo-emitter of the PHHM is a thermal emitter consisting of an electrically heated element, the temperature of which is stabilised by means of a feedback loop in which the temperature of the element is found by measuring the electrical resistance of the element and the current through the element adjusted so as to maintain a constant resistance. Preferably, the processing means of the PHHM, which may be part of a PHHCD, is adapted to carry out the analysis and control to implement the feedback loop.

The light from the photo-emitter may be focused by two curved mirrors onto the cells, after each of which is located a shutter. The processing means is adapted to operate the shutters to select through which shutter the light that illuminates the body part has passed, after which the light is detected by the or each photo-detector. The or each shutter may be mechanical or electro-optical devices such as liquid crystals.

The light from the or each photo-emitter may be transmitted to the body part by means of fibre-optics so as to allow the optical and electrical components to be conveniently remote from the body part. The light penetrates the body part, is scattered or transmitted by the tissue and blood vessels within the body part and may be then collected by one or more further fibre optic devices.

It is apparent that the cells and the elements used to direct the light through them may be located before or after the light passes through or is scattered by the body part.

The cells may comprise areas on a rotating disc interposed between the or each photo-emitter and the or each photo-detector. Some areas of the rotating disc will be coated with analyte or adapted to mimic the absorption spectrum of the analyte and other areas may be uncoated or may be coated by a material with a different absorption spectrum from that of the analyte. In this case, the processor of the PHHM is adapted to co-ordinate the signals received from the or each photo-detector with the rotational position of the disc. This allows the PHHM to employ a single photo-detector and to reduce the complexity of the optical parts, but at the expense of introducing a moving part.

The non-analyte and analyte cells as illustrated in FIGS. 1 and 2 may be replaced by multiple such cells so as to minimise the errors caused if the light is not perfectly collimated and takes different paths through or to and from the body part. Multiple photo-detectors may be employed or the light through more than one non-analyte cell may be collected by one photo-detector and the light through more than one analyte cell be similarly collected.

WO 2013/001265 discloses a PHHM which is adapted to differentiate between signals when the body part is present from signals when it is not. It also discloses a way in which the properties of an artery during the pulse cycle may be exploited. It is well-known that the luminal area of an artery varies as a function of the pressure difference between the arterial blood pressure and the pressure imposed on the artery wall by the surrounding tissue. This is the principle of the Riva-Rocci sphygmomanometer. This is the basis of the disclosure in WO 2013/001265. In addition, the magnitude of the change of luminal area is greatest when the imposed pressure is close to or slightly greater than the diastolic blood pressure in the artery.

Preferably, the PHHM of the present invention includes a means for applying pressure to the body part in the region of an artery, a means for measuring the change in luminal area with each pulse and a means for adjusting the imposed pressure so as to approximate to diastolic blood pressure and thus maximise the change in luminal area. The processor of the PHHM is adapted to detect the difference between the signals from the photosensor when the artery is patent (i.e. at systole when the artery is expanded because the arterial pressure exceeds the imposed pressure) and those when it is occluded (i.e. at diastole when the artery is collapsed because the arterial pressure is less than the imposed pressure).

The signal analysis of the PHHM of this preferred aspect of the invention is thus coherent with the user's pulse.

According to a third aspect of the present invention, there is provided a personal hand-held monitor (PHHM) comprising a signal acquisition device for acquiring signals which can be used to derive a measurement of a parameter related to the health of the user, wherein the signal acquisition device comprises a blood photosensor having one or more photo-emitters for transmitting light to a body part of a user, one or more photo-detectors for detecting light transmitted through or scattered by the body part and two or more optical cells, at least one of which contains an analyte to be detected or which mimics the absorption spectrum of the analyte to be detected, through which the light that has been or will be transmitted through or scattered by the body part passes before it reaches the or each photo-detector, wherein the processor of the PHHM is adapted to process the signals received from the or each photo-detector to calculate the difference in intensity of light which has passed through the or each analyte cell and light which has passed through the or each non-analyte cell, to determine the pulse of the user and to correlate the signals obtained from the photosensor with the pulse of the user, wherein the PHHM is adapted to apply pressure to the body part or to have pressure applied to it by the body part so that, in use, an artery in the body part changes from occluded to patent during each pulse and the processor of the PHHM is adapted to derive a measurement of the change in the luminal area of the artery during each pulse and to correlate the signals received from the blood photosensor with the pulse and the change in the luminal area of the artery to provide a measurement of the concentration of the analyte in the arterial blood.

The means for applying an external pressure to the body part and means for detecting the change in luminal area on each pulse may comprise optical sensors as described in WO 2013/001265.

Preferably the processing means of the PHHM is further adapted to provide audible or visual feedback to the user so that the external pressure may be applied and maintained by the actions of the user, either by pressing the PHHM against the body part or the body part against the PHHM.

This preferred feature of the invention has the benefit of simplifying the way of making measurements but also ensures that the difference between the signals that is measured depends effectively only on the quantity of analyte in the arterial blood and not on that in the surrounding tissue.

Preferably, the or each photo-detector is an InGaAs photo-detector. These offer improved signal to noise ratio over the photo-detectors proposed previously.

The signal obtained from the difference between the signals obtained from the non-analyte and analyte cells, or from the different windows of the rotating disc, must be normalised to estimate the concentration of analyte in the arterial blood. This normalisation may be non-linear. Preferably, the normalisation takes account of the amplitude of the signal from each cell, both with the artery patent and with it occluded, and the amplitude of the signal when the body part is absent. Preferably, it further takes account of the amplitude of the signal indicative of the luminal area to find the concentration of the analyte rather than the total quantity within the field of view of the sensor. Preferably, the processor of the PHHM is adapted to process signals received from the photosensor when the or each photo-emitter is turned off or the light emitted therefrom is completely blocked to compensate signals received when the light from the photo-emitter illuminates the body part for ambient light.

The present invention is described below with reference to the accompanying drawings by way of example only. The invention is not limited to the embodiments shown in the accompanying drawings. The scope of the invention is defined in the accompanying claims.

Figure 3:
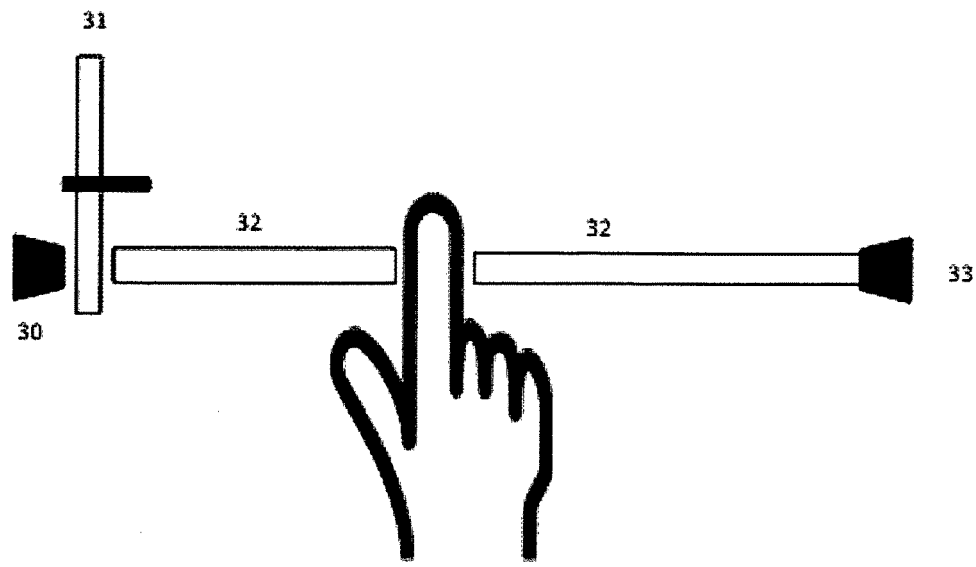
FIG. 3 shows an arrangement of an optical sensor using a rotating disc.

In one embodiment of the PHHM of the present invention, as shown in FIG. 3, a rotating disc (31) is interposed between a thermal emitter (30) and the photo-detector (32). The light is carried by fibre-optics (32). Alternating areas of the rotating disc are coated with the analyte and the others are left clear or coated with a material with a different absorption spectrum from that of the analyte. The instantaneous orientation of the rotating disc (31) is communicated to the processor of the PHHM together with the signal from the photo-detector. The processor is adapted to detect the amplitude of the signal from the photo-detector coherently with the rotation of the disc.

Figure 1:
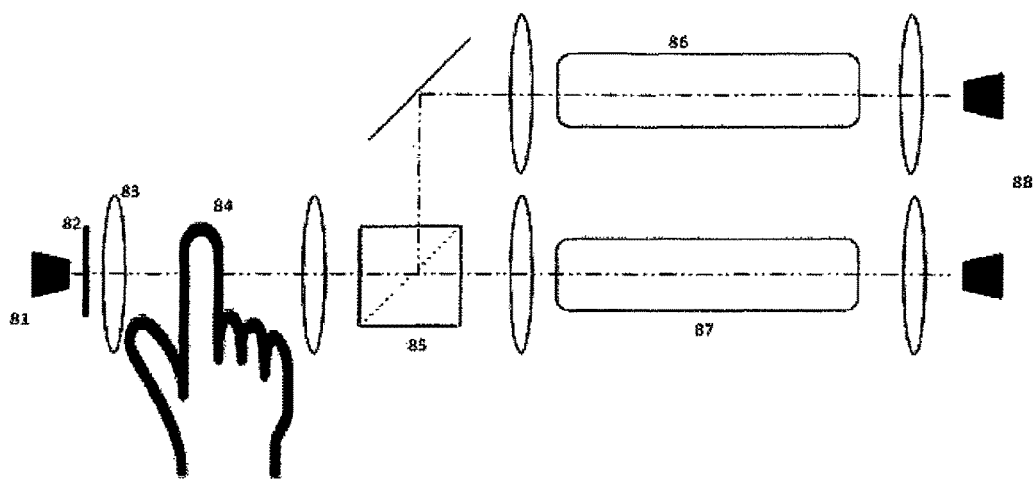
FIGS. 1 and 2 show arrangements for an optical sensor to be used in a PHHM as disclosed in WO 2103/001265.
Figure 2:
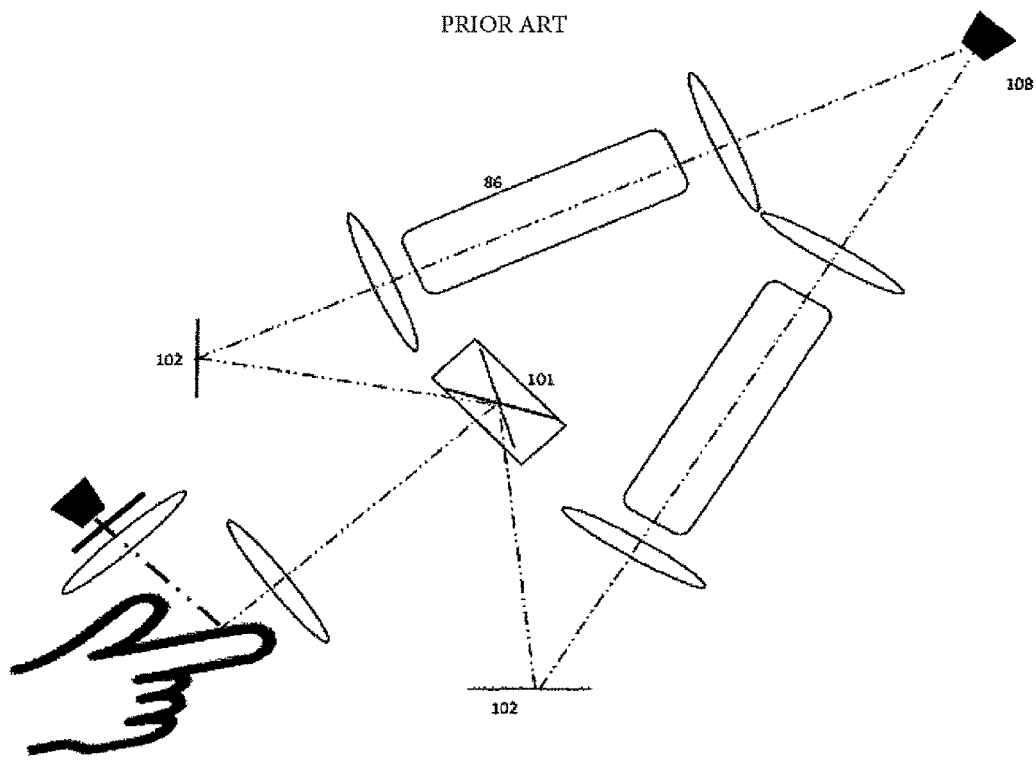

In another embodiment, the non-analyte and analyte cells as illustrated in FIGS. 1 and 2 are replaced by multiple such cells so as to minimise the errors caused if the light is not perfectly collimated and takes different paths through the body part. Multiple photosensors may be employed or the light through more than one non-analyte cell may be collected by one photosensor and the light through more than one analyte cell be similarly collected.

Figure 4:
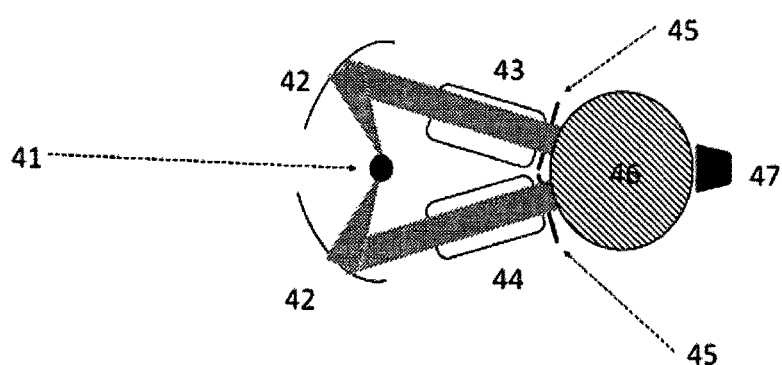
FIG. 4 shows an arrangement of an optical sensor using a thermal emitter.
Figure 5:
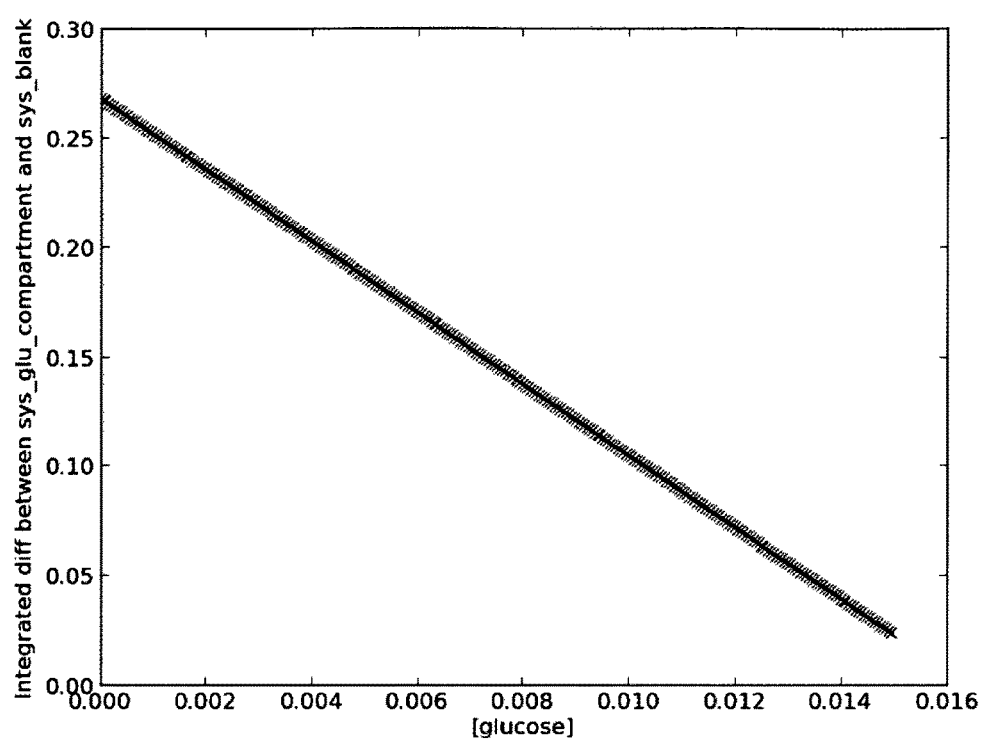
FIG. 5 shows a graph derived from a mathematical model of the performance of an embodiment of the invention.

In another embodiment, shown in FIG. 4, light from a thermal emitter (41) is focused by two curved mirrors (42) onto the cells (43 and 44), after each of which is located a shutter (45). The processing means is adapted to operate the shutters to select through which shutter the light that illuminates the body part (46) has passed, after which the light is detected by the photo-detector (47). The shutter(s) may be mechanical or electro-optical devices such as liquid crystals.

The invention claimed is:

1. A personal hand-held monitor (PHHM) comprising a signal acquisition device for acquiring signals, wherein the signal acquisition device comprises:
a blood photosensor having one or more photo-emitters for transmitting light to a body part of a user,
one or more photo-detectors for detecting light transmitted through or scattered by the body part and two or more optical cells, at least one of which contains an analyte to be detected or which mimics the absorption spectrum of the analyte to be detected, through which the light that has been or will be transmitted through or scattered by the body part passes before the light reaches the or each photo-detector, and at least one of which is a non-analyte cell,
wherein the processor of the PHHM is adapted
to process signals received from the or each photo-detector to calculate the difference in intensity of light which has passed through the or each analyte cell and light which has passed through the or each non-analyte cell,
to determine the pulse of the user and to correlate the signals obtained from the or each photo-detector with the pulse of the user, wherein the PHHM is adapted to apply pressure to the body part or to have pressure applied to the PHHM by the body part so that, in use, an artery in the body part changes from occluded to patent during each pulse and the processor of the PHHM is adapted to derive a measurement of the change in the luminal area of the artery during each pulse and to correlate the signals received from the blood photosensor with the pulse and the change in the luminal area of the artery to provide a measurement of the concentration of the analyte in the arterial blood.

2. The PHHM of claim 1, wherein the PHHM is adapted to be pressed against the body part or to have the body part pressed against the PHHM by a user to vary the luminal area of the artery.

3. The PHHM of claim 2, wherein the processor of the PHHM is adapted to provide visual and/or audible instructions to the user to vary the pressure applied to or by the body part so that the change in luminal area of the artery with each pulse is maximised.

4. The PHHM of claim 1, wherein the or each photo-emitter is a thermal emitter.

5. The PHHM of claim 4, wherein the temperature of each photo-emitter is controlled by means of feedback that regulates the current through or voltage across the photo-emitter.

6. The PHHM of claim 1, wherein the light is transmitted to and/or from the body part by means of fibre-optics.

7. The PHHM of claim 1, wherein the processor of the PHHM is adapted to normalise the calculated difference between the signals from the photosensor by taking account of the measured value of each of those signals, the signal from the photo-detector when the photo-emitter is completely attenuated, similar signals from the photosensor when the body part is not present and any signals derived from the means used to detect the change in luminal area of the artery.

8. The PHHM of claim 1, wherein the cells comprise a rotating disc, one or more parts of which are coated with or carry in solution the analyte or which mimic the absorption spectrum of the analyte and the other parts of which do not.

9. The PHHM of claim 1, wherein one or more shutters are used to select the path of the light through the blood photosensor.

10. The PHHM of claim 9 wherein the optical shutters are electro-optical devices.

11. The PHHM of claim 1, wherein the or each photo-detector is formed of InGaAs.

12. The PHHM of claim 1, wherein the analyte is glucose, ethanol, haemoglobin, creatinine or cholesterol.

13. The PHHM of claim 1, wherein the analyte is an illegal or otherwise forbidden drug or stimulant.

14. The PHHM of claim 1, which includes an electrical sensor comprising at least a first and a second electrode which are electrically isolated from one another and which are arranged to be contacted by two separate parts of the user's body and the processor of the PHHM is adapted to analyse the signals from the electrical sensor to determine the pulse of the user.

15. The PHHM of claim 1, which is self-contained and includes a processor, display and control, communications and storage means to provide a measurement of the concentration of the analyte in the user's blood.

16. The PHHM of claim 1, wherein the signal acquisition device is integrated with a personal hand-held computing device (PHHCD).

* * * * *